United States Patent [19]

Negishi

[11] Patent Number: 5,902,580
[45] Date of Patent: May 11, 1999

[54] CONTROLLING CYPERUS WEEDS WITH ASCOCHYTA SP. FERM BP-5176

[75] Inventor: Hideaki Negishi, Tochigi, Japan

[73] Assignee: Japan Tobacco Inc., Tokyo, Japan

[21] Appl. No.: 08/836,033

[22] PCT Filed: Sep. 11, 1996

[86] PCT No.: PCT/JP96/02584

§ 371 Date: May 14, 1997

§ 102(e) Date: May 14, 1997

[87] PCT Pub. No.: WO97/11158

PCT Pub. Date: Mar. 27, 1997

[30] Foreign Application Priority Data

Sep. 18, 1995 [JP] Japan .................... 7-238906

[51] Int. Cl.$^6$ .............. A01N 5/00; A01N 63/00; C07G 17/00; C12N 1/14
[52] U.S. Cl. .......... 424/93.5; 424/405; 435/171; 435/254.1; 435/267; 435/911
[58] Field of Search ................. 424/405, 93.5; 435/171, 254.1, 267, 911

[56] References Cited

U.S. PATENT DOCUMENTS 4,808,207 2/1989 Gotlieb et al. .............. 71/73

FOREIGN PATENT DOCUMENTS 0296057 12/1988 European Pat. Off. .

OTHER PUBLICATIONS

Stierle et al, Phytochemistry, vol. 30, No. 7, pp. 2191–2192 (1991).

Upadhyay et al, Can. J. Bot., vol. 69, pp. 797–802 (1991).

*Primary Examiner*—David M. Naff
*Assistant Examiner*—Deborah K. Ware
*Attorney, Agent, or Firm*—Birch, Stewart, Kolasch & Birch, LLP

[57] ABSTRACT

The disclosed invention is a method for controlling weeds belonging to the genus Cyperus comprising applying a herbicidal composition containing strain Ascochyta sp. FERM BP-5176 to the weeds in a field. The composition protects crops such as rice, wheat, maize, egg-plant, soybean, cabbage and cucumber in the field. Further, the weed belonging to the genus Cyperus encompasses the species *Cyperus microiria, Cyperus serotinus, Cyperus difformis* or *Cyperus brevifolia* var. *leiolepsis*.

11 Claims, No Drawings

CONTROLLING CYPERUS WEEDS WITH ASCOCHYTA SP. FERM BP-5176

TECHNICAL FIELD OF THE INVENTION

The present invention relates to a novel strain belonging to the genus Ascochyta and a herbicide and a weed control method using a microorganism belonging to the genus Ascochyta.

BACKGROUND ART

As a method for controlling those weeds belonging to the genus Cyperus in Cyperaceae which are major weeds growing in the paddy fields and fields, a method using chemical herbicides is mainly employed. Recently, in view of the problem of environmental pollution caused by abundant use of agricultural chemicals, the development of herbicides not depending on agricultural chemicals and methods for using the same is desired In particular, the development of microbial herbicides using a plant pathogenic fungus are highly expected. To date, DeVine (U.S.A.; target weed: Stranglervine, Asclepiadaceae), Collego (U.S.A.; target weed: Northern jointvetch, Leguminosae) and BioMal (Canada; target weed: Round-leaved mallow, Malvaceae) have been registered as herbicides and commercialized. However, there has not been developed a microbial herbicide targetted at weeds belonging to the genus Cyperus in Cyperaceae.

PROBLEM FOR SOLUTION BY THE INVENTION

It is an object of the present invention to provide a means to control weeds such as cyperaceous plants with a microorganism.

DISCLOSURE OF THE INVENTION

As a result of extensive and intensive research toward the solution of the above assignment, the present inventors have found that a microorganism belonging to the genus Ascochyta has an excellent control ability against weeds such as cyperaceous plants. Thus, the present invention has been achieved.

The present invention relates to the Ascochyta sp. JTKA-644 strain which exhibits pathogenicity against plants belonging to the genus Cyperus.

The present invention also relates to a herbicide comprising, as an active ingredient, a microorganism belonging to the genus Ascochyta which exhibits pathogenicity against weeds.

Further, the present invention relates to a method for controlling weeds using the herbicide described above.

Hereinbelow, the present invention will be described in detail.

First, the novel strain of the invention, Ascochyta sp. JTKA-644, will be described. This strain has been created by collecting diseased weeds of the genus Cyperus in Cyperaceae, isolating those strains which have pathogenicity against the above weeds, pure-culturing them, and examining their control effect against above weeds while using a screening means to examine non-pathogenicity against other crops, particularly rice. The major mycological nature of the novel strain of the invention are enumerated as follows.

The strain is an aerobic fungus and the pH range in which this strain can grow is 3–13, preferably 5–7. The growth temperature is 15–30° C. and the optimum growth temperature is 25–30° C. Its growth on a potato dextrose agar medium is vigorous. The colony generates a large number of black fine particles radiating in all directions and then gradually swirling in white hyphae, and the quantity of aerial hyphae is small. The conidium is colorless, divided into two cells and oval in shape. The size of the conidium is approximately 13–18 µm x approximately 4–6 µm.

As a result of the search of "Illustrated Plant Fungi", (Kobayashi et al., 1992, pp. 2–52, 384, Association of Education for Agricultural Villages) and "Illustrated Genera of Imperfect Fungi", Fourth Edition (Barnett, H. L. and Hunter, B. B., 1987, pp. 6–39, 178, Macmillan Publishing Company) for the above-mentioned mycological nature, the inventors have identified the present strain as a microorganism belonging to the genus Ascochyta. Furthermore, since no Ascochyta microorganism exhibiting pathogenicity against plants of the genus Cyperus in Cyperaceae has been known though some Ascochyta microorganism are known as pathogenic fungi against cucumber, tomato and the like, the present strain has been recognized as a novel strain and designated Ascochyta sp. JTKA-644 strain. This strain was deposited with the National Institute of Bioscience and Human-Technology, Agency of Industrial Science and Technology (1–3, Higashi 1-Chome, Tsukuba City, Ibaraki Pref., Japan) under accession number FERM BP-5176 (date of original deposit: Jul. 21, 1995).

No special method is required for the fermentation of the present strain. A method similar to that used in the fermentation of known Ascochyta strains may be used. As a medium, either a synthetic or natural medium may be used as long as it appropriately contains assimilable carbon sources, nitrogen sources, minerals and necessary growth promoting substances. As examples of specific media, potato dextrose agar medium (PDA), Czapek agar medium and the like may be enumerated. In the fermentation, it is desirable to maintain the temperature at 15–30° C., preferably 25–30° C. and to maintain the pH at 3–13, preferably 5–7. When the strain has been cultured for about 7– 14 days under the conditions described above, a sufficient quantity of conidia are formed on the surface of the medium The present strain kills those weeds belonging to the genus Cyperus in Cyperaceae which are weeds growing in paddy fields. On the other hand, the present strain does not affect gramineous crops such as rice, wheat, barley, maize and the like nor other crops such as egg-plant, soybean, cabbage, cucumber and the like. This strain is capable of mass culture and, at the same time, a large quantity of spores can be obtained easily.

Now, the herbicide and the control method of the invention will be described below.

As a microorganism to be used in the herbicide of the invention, the Ascochyta sp. JTKA-644 strain may be given. In addition to this strain, any microorganism belonging to the genus Ascochyta and exhibiting pathogenicity against plants belonging to the genus Cyperus may be used. The herbicide of the invention may be formulated by suspending in water spores obtained by mass-culturing a microorganism belonging to the genus Ascochyta, but the formulation method is not limited to this one. In this method, the spore concentration is appropriately $10^6$–$10^7$ spores/ml but not limited to this range. In suspending spores in water, adjuvants such as a surfactant and a spreader may be added. The microorganism which is the major agent may be a fresh microorganism immediately after fermentation. Alternatively, a once stored microorganism may be used after renaturing with water or the like. As a method for storing, well known methods for storing microorganisms such as ultra low temperature storing (–80° C.), vacuum lyophilization or the like may be used.

The control method of the invention is performed by applying the herbicide described above to a field. The amount of application may be decided depending of the degree of luxuriant growth of weeds. Usually, it is desirable to apply the herbicide at a rate of $10^{11}$–$10^{12}$ pores per 10 a. of the field.

The target plants of the herbicide and the control method of the invention are not particularly limited, but they are especially effective against plants belonging to the genus Cyperus. Also, the stage of growth of the target plant is not particularly limited. The herbicide and the control method of the invention are applicable to a wide range of plants from those which have just germed to those which are grown-up.

EXAMPLES

1) Process of Creation of the Novel Strain of the Invention

Weeds of the genus Cyperus in Cyperaceae growing in paddy fields or fields and exhibiting a disease symptom were collected, and the diseased portions were cut off. The cut off pieces of leaves were immersed in 70% ethanol solution for 30–60 seconds, then suspended in a solution prepared by adding to 1% sodium hypochloride solution an equal volume of 0.1% Tween 80 solution and immersed for 1–3 minutes to sterilize the surface. Subsequently, the leaf pieces were washed with 0.1% Tween 80 solution once and with sterilized water twice. Thereafter, the leaf pieces were placed on PDA medium containing antibiotics and cultured in a incubator at 25° C. for 2–5 days. The fringe portions of elongated colonies were transferred to fresh PDA medium to allow the formation of conidia. Further, the conidia were streaked onto fresh PDA medium and cultured to thereby obtain a single colony. Thus, the pure isolation of the microorganism was performed.

For each of the isolated stains, pathogenicity against weeds of the genus Cyperus in Cyperaceae was re-examined and influence upon rice, wheat, maize, tomato and cucumber was also examined. As a result, the novel strain Ascochyta sp. JTKA-644 was isolated which reveals an excellent herbicidal effect and does not affect rice, wheat, maize, tomato nor cucumbers.

2) Identification of the Created Strain

The identification of the strain of the invention was performed by mainly observing the morphology of the conidia. As a result, the strain was identified as a microorganism belonging to the genus Ascochyta, as described previously.

3) Methods for Mass Culture and Formulation

It has become possible to inoculate a large quantity of a microorganism into a Petri dish (9 cm in diameter) at one time by adding sterilized water to a microorganism belonging to the genus Ascochyta grown on PDA medium and agitating to thereby prepare a spore suspension of a high concentration, dripping about 100 μl of this suspension to V-8 juice agar medium and then dispersing the suspension with a sterilized L-shaped glass rod. As a result, the yield of spores was about $6 \times 10^7$ spores per Petri dish.

As described above, a large quantity of spores can be obtained from the microorganism of the invention easily by plate culture.

Subsequently, the spores obtained may be formulated into a wettable powder by suspending them in 10% skim milk and vacuum drying.

The thus obtained wettable powder may be applied to weeds after it is suspended in water and a surfactant such as Tween 80 is added thereto.

4) Pathogenicity Test against *Cyperus microiria*

*Cyperus microiria* was grown in a commercial pot, and plants at 2- to 5-leaf stage were used as test samples.

The microorganism of the invention was cultured on a potato agar medium, and spores obtained were suspended in 0.1% Tween 80 solution to give a concentration of $10^4$ spores/ml to $10^7$ spores/ml. The resultant suspension was inoculated to *Cyperus microiria* with an air spray. The samples were immediately placed in a moist chamber and left for 48 hours. Then, the samples were transferred to a green house of 25° C. Two weeks thereafter, the incidence of disease on *Cyperus microiria* and the percent control were surveyed. At a concentration of $10^7$ spores/ml, the incidence of disease by the microorganism of the invention on *Cyperus microiria* was 100%; the percent of killed *Cyperus microiria* by the microorganism of the invention was 100%; and the percent control of *Cyperus microiria* by the microorganism of the invention was 100%.

TABLE 1

Control Effect of the JTKA-644 Strain against *Cyperus microiria*

| Spore Concentration | Incidence of Disease | Percent killed | Percent Control (%) |
|---|---|---|---|
| 0 | 0 | 0 | 0 |
| $10^4$ | 0 | 0 | 0 |
| $10^5$ | 100 | 0 | 5 |
| $10^6$ | 100 | 0 | 70 |
| $10^7$ | 100 | 100 | 100 |

*Incidence of disease: Number of diseased plants/Number of inoculated plants × 100
*Percent killed: Number of killed plants/Number of inoculated plants × 100
*Percent control: Ratio of reduction in plants as a whole (farsighted view)

As is clear from Table 1, the microorganism of the invention exhibited an excellent control effect against *Cyperus microiria* at a concentration of $10^7$ spores/ml.

5) Pathogenicity Test against Weeds Belonging to the Genus Cyperus

A pathogenicity test against weeds of the genus Cyperus was performed in a manner similar to that employed in the pathogenicity test against *Cyperus microiria*. The spore concentration in the inoculum was $10^7$ spores/ml.

As test plants, *Cyperus microiria*, *Cyperus serotinus*, *Cyperus brevifolia* var. *leiolepis* and *Cyperus difformis* were used. The test results are shown in Table-2.

TABLE 2

Control Effect of the JTKA-644 Strain against Weeds of the Genus Cyperus

| Plant | Presence or Absence of Effect |
|---|---|
| *Cyperus microiria* | + |
| *Cyperus serotinus* | + |
| *Cyperus brevifolia* var. *leiolepis* | + |
| *Cyperus difformis* | + |

+: Killing or growth inhibition
−: No influence

As is clear from Table-2, the microorganism of the invention exhibited an excellent control effect against weeds of the genus Cyperus.

6) Influence on Crops

A pathogenicity test against crops was performed in a manner similar to that employed in the pathogenicity test against *Cyperus microiria*. The spore concentration in the inoculum was $10^7$ spores/ml.

As test plants, rice, wheat, maize, tomato and cucumber were used. The test results are shown in Table-3.

TABLE 3

| Influence on Crops | |
|---|---|
| Plants | Presence or Absence |
| Rice | – |
| Wheat | – |
| Maize | – |
| Egg-plant | – |
| Soybean | – |
| Cabbage | – |
| Cucumber | – |
| *Cyperus microiria* | + |

+: killing or growth inhibition
–: No influence

As is clear from Table-3, the microorganism of the invention did not give any influence upon the growth of rice, wheat, maize, egg-plant, cucumber, cabbage and soybean.

[Formulation Example 1] (Liquid Formulation)

Conidia from the Ascochyta sp. JTKA-644 strain ($10^{10}$ conidia) and Tween 80 (1 g) were added to 1 L of water and mixed to thereby prepare a liquid formulation.

[Formulation Example 2] (Wettable Powder)

$10^8$ conidia from the JTKA-644 strain were suspended per 1 ml of a mixed solution consisting of maltose (9%), clay (1%) and water (90%). This suspension was air-dried, and then the dried material was mixed and crushed to thereby prepare a wettable powder.

[Formulation Example 3] (Wettable Powder) $10^8$ conidia from the JTKA-644 strain were suspended per 1 ml of a mixed solution consisting of skim milk (10%) and water (90%). This suspension was vacuum-dried, and then the dried material was mixed and crushed to thereby prepare a wettable powder.

[Formulation Example 4] (Dust Formulation) $10^8$ conidia from the JTKA-644 strain were mixed per 1 g of a mixture consisting of hydroxypropyl-β-cyclodextrin (14%), white carbon (12%) and clay (74%). The resultant mixture was dried and crushed uniformly to thereby prepare a dust formulation.

[Formulation Example 5] (Granules)

$10^8$ conidia from the JTKA-644 strain were added per 1 g of a mixture consisting of β-cyclodextrin (15%), starch (2%), bentonite (18%), calcium carbonate (36%) and water (29%) and kneaded. Then, the kneaded material was formed into granules with a granulator and dried. Thus, granules were prepared.

[Formulation Example 6] (Emulsifiable Concentrate)

$10^8$ conidia from the JTKA-644 strain were added per 1 g of a mixture consisting of ammonium polyoxyethylene nonylphenyl ether phosphate (18%), polyoxyethylene nonylphenyl ether (6%), triethyl phosphate (29%) and tributyl phosphate (47%) and suspended homogeneously to thereby obtain an emulsifiable concentrate.

[Formulation Example 7] (Oil Formulation)

In 1 ml of a mixed solution consisting of spindle oil (95%), castor oil (4%) and silicone oil (1%), $10^8$ conidia from the JTKA-644 strain were suspended to thereby prepare an oil formulation.

[Formulation Example 8] (Dry Flowable)

In 1 ml of a composition consisting of sodium alkylbenzenesulfona te (12%) and polyethylene glycol ether (88%), $10^8$ conidia from the JTKA-644 strain were suspended to thereby prepare a dry flowable.

[Formulation Example 9] (Capsules)

In 1 ml of a mixed solution consisting of sodium alginate (0.7%), kaolin (5%), glycerol (15%) and water (79.3%), $10^8$ conidia from the JTKA-644 strain were suspended. The suspension was dripped to 0.2 M calcium acetate solution to thereby obtain a capsule-like product. This product was cut into pieces, sieved and air-dried to thereby prepare capsules.

EFFECT OF THE INVENTION

The herbicide of the invention selectively kill weeds belonging to the genus Cyperus in Cyperaceae or inhibit the growth thereof to thereby control those weeds without affecting crops such as rice. Further, unlike agricultural chemicals, the herbicide of the invention does not pollute nor destroy the environment.

I claim:

1. A biologically pure culture of Ascochyta sp. FERM BP-5176 which exhibits pathogenicity against weeds belonging to the genus Cyperus.

2. A herbicidal composition comprising:

a biologically pure culture of Ascochyta sp. FERM BP-5176 which exhibits selective pathogenicity against weed belonging to the genus Cyperus and an agriculturally acceptable carrier.

3. The herbicidal composition of claim 2, wherein the weed belonging to the genus Cyperus is any one of *Cyperus microiria, Cyperus serotinus, Cyperus difformis* or *Cyperus brevifolia* var. *leiolepsis*.

4. The herbicidal composition according to claim 2 wherein said composition is in the form of a powder or a suspension.

5. The herbicidal composition of claim 4, wherein said powder is a wettable powder.

6. The herbicidal composition of claim 4, wherein said suspension is an aqueous suspension.

7. The herbicidal composition of claim 6, wherein said aqueous suspension further comprises a surfactant.

8. A method for controlling weeds comprising applying a herbicidally effective amount of a herbicide comprising Ascochyta sp. FERM BP-5176 to a field containing weeds belonging to the genus Cyperus.

9. The method of claim 8, wherein said field is a paddy field.

10. The method of claim 8, wherein said herbicide is applied to said field having a crop selected from the group consisting of rice, wheat, maize, egg-plant, soybean, cabbage and cucumber.

11. The method of claim 8, wherein the weed belonging to the genus Cyperus is any one of *Cyperus microiria, Cyperus serotinus, Cyperus difformis* or *Cyperus brevifolia* var. *leiolepsis*.

* * * * *